United States Patent
Cheng et al.

(10) Patent No.: US 6,979,576 B1
(45) Date of Patent: Dec. 27, 2005

(54) METHODS OF USE OF ONE STEP IMMUNOCHROMATOGRAPHIC DEVICE FOR STREPTOCOCCUS A ANTIGEN

(76) Inventors: Shu-Ching Cheng, 6150 Lago Lindo, Rancho Santa Fe, CA (US) 92067; Ching Huang, 635 Indigo Canyon Rd., Chula Vista, CA (US) 91911; Ming-Shian Wu, 2139 Calle Guaymas, La Jolla, CA (US) 92037; Michael J. Willrodt, 157 Avacado Crest La., Escondido, CA (US) 92025; Herbert Bradfield Cunningham, 6535 Engineers Rd., Julian, CA (US) 92036; Eugene Fan, 7813 Esterel Dr., La Jolla, CA (US) 92037

(*) Notice: Subject to any disclaimer, the term of this patent is extended or adjusted under 35 U.S.C. 154(b) by 0 days.

(21) Appl. No.: 08/900,559

(22) Filed: Jul. 25, 1997

(51) Int. Cl.[7] ............ G01N 33/569; G01N 33/53; G01N 33/543; G01N 33/537
(52) U.S. Cl. ............ 436/807; 435/7.34; 435/7.92; 435/7.96; 435/283.1; 435/286.5; 435/287.1; 435/287.2; 435/287.3; 435/287.7; 435/288.3; 435/288.4; 435/288.5; 435/308.1; 436/174; 436/177; 436/514; 436/518; 436/532; 436/538; 436/810
(58) Field of Search ............ 435/7.34, 7.92, 435/7.94, 961, 970, 283.1, 286.5, 287.1, 287.2, 287.3, 287.7, 288.3, 288.4, 288.5, 308.1; 436/514, 518, 532, 538, 174, 177, 807, 810

(56) References Cited

U.S. PATENT DOCUMENTS

| | | | | |
|---|---|---|---|---|
| 3,957,436 A | * | 5/1976 | Murray | 436/513 |
| 4,059,407 A | * | 11/1977 | Hochstrasser | 23/253 |
| 4,859,610 A | * | 8/1989 | Maggio | 436/518 |
| 4,861,711 A | * | 8/1989 | Friesen et al. | 436/518 |
| 4,943,522 A | * | 7/1990 | Eisenger et al. | 435/7.92 |
| 5,177,024 A | * | 1/1993 | Chan et al. | 436/536 |
| 5,415,994 A | * | 5/1995 | Imrich et al. | 435/7.34 |
| 5,494,801 A | * | 2/1996 | Bogart et al. | 435/7.34 |
| 5,604,109 A | * | 2/1997 | Fischetti et al. | 435/7.34 |
| 5,712,172 A | * | 1/1998 | Huang et al. | 436/518 |

* cited by examiner

*Primary Examiner*—Lynette R. F. Smith
*Assistant Examiner*—JaNa Hines

(57) ABSTRACT

A method to determine the presence or absence of Streptococcus Group A antigen in a sample, comprising the following steps: extracting the antigen from the sample in an assay chamber with two or less extraction reagents, wherein the two reagents may be added to the assay chamber in no particular sequence; introducing a lateral flow immunochromatographic assay device into the extraction reagents containing the extracted antigen without further addition of reagents or manipulation of the sample; forming an antigen-indicator labeling reagent complex; and determining the presence or absence of the antigen in the sample by the presence or absence of a signal formed by the binding of the antigen-indicator labeling reagent complex to an indicator capture reagent specific for said antigen-indicator labeling reagent complex.

12 Claims, 4 Drawing Sheets

METHODS OF USE OF ONE STEP IMMUNOCHROMATOGRAPHIC DEVICE FOR STREPTOCOCCUS A ANTIGEN

BACKGROUND OF THE INVENTION

This invention relates to immunological methods and devices for detecting analytes in biological samples.

Numerous approaches have been developed for detection of a given analyte in a biological sample. Typical of these methods are the so called "lateral flow" and "flow-through" devices and methods. The flow-through device generally uses a porous material with a reagent-containing matrix layered thereon or incorporated therein. Test sample is applied to and flows through the porous material, and analyte in the sample reacts with the reagent(s) to produce a detectable signal on the porous material. These devices are generally encased in a plastic housing or casing with calibrations to aid in the detection of the particular analyte.

Lateral flow assays also utilize a porous membrane for performing analyte detection. Instead of drawing the sample through the membrane perpendicularly, the sample is permitted to flow laterally from an application zone to a reaction zone on the membrane surface. The capture reagent is present in the reaction zone, and the captured analyte can be detected by a variety of protocols, including direct visualization of visible moieties associated with the captured analyte.

One-step lateral flow assays permit a user to add a sample to a sample application region and obtain a positive or negative signal signaling the presence or absence of the test analyte in the sample.

One-step lateral flow devices contain a sample application region to which the liquid sample is applied. The sample application region is in lateral flow contact with the porous carrier material of the analyte detection region. During lateral flow, the sample is brought into contact with a mobile indicator reagent in a discrete zone of the analyte detection region. The indicator reagent contains both a binding moiety which specifically binds to the target analyte and an indicator moiety, which is most often a chromophore label. Target analyte molecules moving in the lateral flow bind to the indicator reagent and are ultimately immobilized in the capture zone, usually by binding to a second reagent which binds specifically to the analyte or to the analyte-indicator reagent complex, giving rise to a positive test signal. Additional signals may include a negative reaction indicator, a test complete indicator, and a positive control indicator.

One-step immunochromatographic devices containing the indicator reagent in a discrete zone of the lateral flow-porous material, e.g., at a discrete site on the test strip, have been described.

Lateral flow assays also utilize a porous membrane for performing analyte detection. Instead of drawing the sample through the membrane perpendicularly, however, the sample is permitted to flow laterally from an application zone to a reaction zone on the membrane surface. The capture reagent is present in the reaction zone, and the captured analyte can be detected by a variety of protocols, including direct visualization of visible moieties associated with the captured analyte.

For example, Hochstrasser, U.S. Pat. No. 4,059,407, discloses a dipstick device which can be immersed in a biological fluid to semi-quantitate analyte in the fluid. Semi-quantitation of the analyte is accomplished by using a series of reagent-containing pads wherein each pad in the series will produce a detectable color (i.e., a positive result) in the presence of an increasing amount of analyte.

In U.S. Pat. Nos. 4,094,647, 4,235,601 and 4,361,537, Deutsch et al. describe immunoassays of certain liquid samples deposited on a chromatographic test strip device. The device comprises a material capable of transporting a solution by capillary action, i.e., wicking. Different areas or zones in the strip contain the reagents needed to produce a detectable signal as the analyte is transported to or through such zones. The device is suited for both chemical assays and binding assays which are typified by the binding reaction between an antigen and its complementary antibody.

Many variations on the Deutsch et al. device have also been disclosed. For example, Grubb et al., U.S. Pat. No. 4,168,146 describes the use of a porous test strip material to which is covalently bound an antigen-specific antibody. In performance of an assay, the test strip is immersed in a solution suspected of containing an antigen, and capillary migration of the solution up the test strip is allowed to occur. As the antigen moves up the test strip it binds to the immobilized antigen-specific antibody. The presence of antigen is then determined by wetting the strip with a second antigen-specific antibody to which a fluorescent or enzyme label is covalently bound. Quantitative testing can be achieved by measuring the length of the strip that contains bound antigen.

In addition, European Publication No. 323,605 discloses an assay device using chromatographic material wherein the test sample can travel from one end to the other by capillary action. The chromatographic material contains an immobilized capture reagent capable of binding to the analyte. The application pad receives the test sample and contains a diffusive indicator reagent capable of migrating from the application pad to the chromatographic material. The indicator reagent is capable of binding to the analyte or the capture reagent. The binding of the indicator reagent results in a detectable signal.

Other disclosures of lateral flow assays have also appeared. For example, U.S. Pat. No. 4,861,711 describes a lateral flow assay wherein all components needed for the detection of an analyte are embedded in a single sheet. The lateral flow is referred to as chromatographic behavior. This patent discloses the use of enzyme antibody conjugates and substrates, each separately held in absorbent pads. European Patent Application 306,772 describes a lateral flow device which comprises a chromatographic medium wherein the zone for application of sample and the reaction zone with an immobilized reagent capable of binding the analyte or a label-specific binding material are separated. British Application No. 2,204,398 describes the use of a lateral flow device for testing hCG in urine samples, where sample applied to the device picks up labeled reagent and permeates into a detection zone. Labels include gold sols and colored particles.

For instance, European Publication No. 323,605 discloses an assay device using chromatographic material wherein the test sample can travel from one end to the other by capillary action. The chromatographic material contains an immobilized capture reagent capable of binding to the analyte. The application pad which receives the test sample also contains a diffusible indicator reagent capable of migrating from the application pad to the chromatographic material. The indicator reagent is capable of binding to the analyte. The binding of the indicator reagent-analyte complex results in a detectable signal at the capture situs.

PCT application No. WO 94/06013 also describes a lateral flow assay in which the indicator reagent has been placed in a separate labeling reagent region or pad (referred to as "the third liquid permeable material"). The sample is added to a separate sample application pad, passes through a second permeable material, and mobilizes the indicator reagent located in the third liquid permeable material. The sample then enters the wicking material containing the capture zone. Patent application WO 92/01226 describes a lateral flow device in which the labeled specific binding reagent is retained in the dry state either in a zone on the carrier material or in a separate porous body through which the sample passes en route to the porous carrier material of the test strip.

U.S. patent application Ser. No. 08/444,238 issued as U.S. Pat. No. 5,712,172 and its corresponding PCT application 96/04748 also describe lateral flow assay devices in which the labeled reagent for the analyte is located in a discrete zone of the porous carrier material of the analyte detection region.

Procedures using chromogenic and fluorescent dyes as labels in biological assay procedures are also known. Typical assay protocols call for direct or indirect binding of a dye label to an analyte or analyte analog in a biological sample, where the presence or absence of the dye at a particular stage of the assay can be determined visually and related to the amount of analyte initially present in the sample. A wide variety of specific assay protocols exist.

A number of those assays utilize naturally colored or dyed particles as a label, where the particles are bound to an antibody or other specific binding substance. Suggested particles include dyed latex beads, dye imbibed liposomes, erythrocytes, metal sols, and the like. The colored particle in such complexes can serve as a visible marker, where separation, capture, or aggregation of the particles is mediated through binding of the antibody or other specific binding substance. The amount of label thus segregated in a particular assay step is related to the amount of analyte initially present in the sample.

U.S. Pat. No. 4,863,875 describes compositions comprising at least ten dye molecules or monomers covalently attached to an antibody through an isocyanate group on the dye. U.S. Pat. No. 4,703,017 describes a solid phase assay device which relies on specific binding of a ligand-label conjugate on a solid support, where the label is disclosed as a particle, such as a liposome, or polymer microcapsule.

For example, U.S. Pat. No. 4,943,522 describes methods of detecting analytes using a solid phase lateral flow assay where the sample is applied to a lateral flow membrane having a pore size of 1–250 microns. PCT Publication WO 92/12428, which is related to the above patent, represents an improvement on that method and device wherein nonbibulous lateral flow is used to conduct visible moieties, especially labeled particles, e.g., dyed latex, red blood cells or liposomes capable of reacting with analyte or a competitor thereto into a capture zone for detection, using a bibulous support made nonbibulous by treatment with a blocking agent. The result is a one-step assay which can be conducted in a very short period of time (typically, within 60 seconds), and wherein the readout is usually available instantaneously upon the sample contacting a capture zone.

Immunoassays have been developed to detect the presence or absence of a variety of analytes including analytes useful in clinical diagnoses, including the diagnosis of Group A Streptococcus.

Group A Streptococcus is one of the most important causes of acute upper respiratory tract infection. Approximately 19% of all upper respiratory tract infections are caused by Group A Streptococci. (Lauer, B. A., et al., J. Clin. Microb., 17:338–340 (1983)). Early diagnosis and treatment of Group A Streptococcal pharyngitis has been shown to reduce the severity of symptoms and further complications such as rheumatic fever and glomerulonephritis. (Youmans, G. P., et al., in The Biologic and Clinical Basis of Infectious Diseases, at 177–183 (W. B. Saunders Co. 1980)). Conventional identification procedures for Group A Streptococcus from throat swabs involve the isolation and subsequent identification of viable pathogens by techniques that require 24 to 48 hours or longer. (Faklam, R. R. and Washington, J. A., Streptococcus and Related Catalase-Negative Gram-Positive Cocci, in Manual of Clinical Microbiology at 238–257 (Balows, A. et al., eds., 5th ed. 1991)). Immunoassays which detect Group A Streptococcal antigens can be performed in less than one hour.

Various immunoassays for the detection of Group A Streptococcus from throat swabs are commercially available. Immunoassays for Group A Streptococcus sold by Applied Biotech, Inc. and Abbott require the transfer/application of a solubilized sample to the immunoassay device and the addition of three reagents in a specific order. In the Abbott test, the throat swab sample is extracted in a mixture of 3 drops of 2.0 M sodium nitrite and 3 drops of 1.0 M acetic acid which are mixed just prior to the extraction procedure. The swab is introduced into this solution, and twirled to obtain mixing. The sample solution is then neutralized with 3 drops of a solution of 1.0 M Tris buffer prior to running the immunoassay. The immunoassay device contains a plastic housing with a sample well into which the extracted sample is poured.

Similarly, in the Applied Biotech test, sold under the trademark "SURESTEP", the throat swab sample is extracted in a mixture of 3 drops of 1.0 M sodium nitrite and 3 drops 1.25 M acetic acid which are mixed just prior to the extraction procedure. After the extraction procedure, the sample mixture is neutralized with 3 drops of a solution of 0.1 M Tris-0.7 M sodium hydroxide prior to running the immunoassay. The immunoassay device contains a plastic housing with a sample chamber into which the extracted sample is pipetted.

In addition, U.S. Pat. No. 5,591,645 describes a solid phase chromatographic immunoassay for detecting Group A streptococcus. The assay requires the use of three reagents which must be added in a specific order, i.e., 0.1 M HCl was added to 4M sodium nitrite to obtain nitrous acid. An aliquot of Group A streptococcus was added to the nitrous acid solution. 1 M Tris base was then added to the sample in order to neutralize the nitrous acid prior to running the immunoassay on a dilution series of samples. The end point of the test was $5 \times 10^5$ organisms/ml.

Such tests requiring the addition of more than two reagents introduce the possibility of user error in the sequence of addition of the reagents, necessitating performance of the test by a skilled worker in order to obtain reliable results.

Other tests which do not require transfer of a sample after extraction have complex housings with an area designed for in-the-device sample extractions. The housing of these tests contain an area designed to receive the swab, and requires use of specially designed swabs which fit precisely into the swab chamber area.

The Binax "NOW" Strep A test consists of a complex folding booklet cardboard housing which contains an area on the inner right side into which the swab is inserted between layers of cardboard. 4 drops of 2 M sodium nitrite with TWEEN 20™ detergent and 4 drops of 0.125 M acetic acid with TWEEN 20™ are then added to the swab area, and the swab is rotated. This requires use of a specially designed swab which will fit into the hole designed to receive the swab. The cardboard housing is then folded, bringing the immunoassay strip, housed in the left inner surface, into contact with the swab.

The Quidel "QUICKVUE" Test contains a complex plastic housing having a specially designed "in-line" swab chamber into which a specially designed swab is inserted. The "QUICKVUE" test contains an extraction solution bottle obtaining 0.6 ml of 4M sodium nitrite with 0.01% Thimerosal, and an internal crushable ampule of 0.65 ml 0.2 M acetic acid. The ampule is crushed to mix the solutions just prior to sample extraction. The throat swab specimen is inserted into the swab chamber, and 8 drops of the freshly mixed solution are added to the swab chamber. As the liquid seeps through the swab, the liquid is carried by capillary action into the test strip. Use of a swab which does not precisely fit into the plastic chamber will result in liquid flow which is too rapid for efficient sample extraction.

These one-step assays are complex devices requiring a number of immunoassay reagents. Moreover, because the geometry of these devices for these one-step assays limits the amount of mixing of the sample with the extraction reagents and/or the time of exposure of the sample to the extraction reagents, these assays have limited sensitivity due to poor extraction of the analyte. Thus, there is a need for a one-step assay which permits thorough mixing of the sample with the extraction reagents, and exposure of the sample to the extraction reagents for a desired length of time. Simplifying the number of reagents added during the performance of the assay and eliminating the need to transfer the sample after extraction is also desirable in an assay for health and safety and regulatory purposes. When two reagents are added to the sample during performance of the assay, simplification can also be obtained if the reagents are not required to be added to the sample in a particular sequence.

Thus, there is still the need to develop an immunoassays for a Strep A antigen extracted or solubilized from samples, where 2 or less sample extraction reagents are added, in no particular sequence, during performance of the assay, and where the sample does not require transfer to the immunoassay device after efficient sample extraction. There is also a need for a one-step assay utilizing devices which do not require complex plastic or cardboard housings or specially designed swabs to obtain sample extraction.

None of the references or products described herein is admitted to be prior art.

SUMMARY OF THE INVENTION

This invention relates to an immunoassay for extracted Streptococcus Group A carbohydrate antigens which can be performed by individuals without extensive training in laboratory techniques. Moreover, these assays do not require transfer of the sample to the immunoassay device following extraction of the antigens.

The lateral flow immunochromatographic assay devices of the present invention do not require the use of elaborate cardboard or plastic casings or specially fitted swabs. Instead commercially available test tubes and swabs may be used with the assays of this invention.

The methods of this invention provide for the detection of analytes in samples which must be extracted prior to running the assay, while minimizing sample manipulation. In a first aspect, this invention relates to: A method to determine the presence or absence of Streptococcus Group A antigen in a sample, comprising the following steps:
  (a) extracting the antigen from said sample in an assay chamber with two or less extraction reagents, wherein said two reagents may be added to said assay chamber in no particular sequence;
  (b) introducing a lateral flow immunochromatographic assay device into said extraction reagents containing said extracted antigen without further addition of reagents or manipulation of said sample;
  (c) forming an antigen-indicator labeling reagent complex; and
  (d) determining the presence or absence of said antigen in the sample by the presence or absence of a signal formed by the binding of said antigen-indicator labeling reagent complex to an indicator capture reagent specific for said antigen-indicator labeling reagent complex.

In a preferred embodiment, the method of this invention further comprises the step of determining the presence of a positive control signal. The positive control signal acts as an internal control that the reagents are functional and the assay has been performed properly.

By stating that the extraction reagents may be added to said assay chamber in no particular sequence means that the order of addition of the extraction reagents will not affect the assay results. One of ordinary skill in the art would recognize that even if one of the extraction reagents contains a color indicator which would make it preferable for the colored reagent to be added to the assay chamber first, the results of the assay will not be affected by the order in which the extraction reagents are added to the assay chamber.

In one preferred embodiment, extraction of the Strep A antigen preferably is carried out by mixing a first solution of sodium nitrite, and a second solution of acid, preferably acetic acid, to obtain nitrous acid in a test tube, inserting a throat swab into the solution, and vigorously mixing the sample with the reagents by turning the throat swab against the side of said test tube. Preferably the concentration of the sodium nitrite solution is 0.2–5 M, while the concentration of the acetic acid solution is preferably 0.02–2 M. More preferably, the extraction is carried out by contacting the throat swab with a freshly prepared solution of nitrous acid. The freshly prepared solution of nitrous acid is preferably made by mixing equal volumes of 2 M sodium nitrite and 0.3 M acetic acid in a test tube, and vigorously turning the swab against the side of the test tube, preferably at least 10 times. After vigorously mixing the sample with the reagents, extraction is allowed to proceed for preferably at least 10 seconds, more preferably for at least 60 seconds to allow adequate extraction of the carbohydrate antigen.

By freshly prepared is meant that the solution must preferably be mixed not more than 30 minutes prior to the extraction of the antigen, more preferably not more than 2 minutes prior to the extraction.

The sodium nitrite solution may also contain a detergent, for example, TWEEN 20™ detergent, or an antibiotic, for example, 0.01% Thimerosal.

In an even more preferred embodiment, a color indicator is added to the solution of 2 M sodium nitrite, so that as the 0.3 M acetic acid solution is added to the solution of 2M sodium nitrite, and the color of the 2M sodium nitrite solution changes from pink to light yellow.

In the assays of this invention, neutralization of the nitrous acid solution is not required following extraction of the antigens prior to running the lateral flow immunochromatographic assay. Preferably the lateral flow immunochromatographic assay device contains a porous sample receiving region member impregnated with buffer which will neutralize the nitrous acid during lateral flow of the sample through the device.

In particular, the invention can be used to detect the presence or absence of the Streptococcus Group A antigen in samples requiring extraction of the antigen, preferably throat swabs.

Thus, the first aspect of the present invention features immunochromatographic assays for the detection of the presence or absence of Strep A antigen in a sample which requires extraction prior to performing the immunochromatographic assay. These one-step assays preferably require addition of two or less immunoassay reagents to the assay chamber.

Because simplifying the number of reagents added to the sample and decreasing manipulation of the sample following extraction is desirable for health and safety and regulatory purposes, it is desirable to develop other design variations that simplify the number of reagents necessary to perform the assay, and which eliminate the need for further sample manipulation following extraction of the antigen in order to decrease the possibility of user error. For instance, further manipulation of the sample can result in mixing or loss of samples during transfer. In addition, use of more than three reagents which must be added to an assay chamber in a specific order can result in errors in the sequence of addition.

Any one-step immunochromatographic assay device can be used in the assays of this invention, including test strip devices or devices having plastic housings. Preferably, the immunochromatographic assay device contains a sample receiving region which is made of a porous material. The porous material conducts lateral flow of the liquid sample. The sample receiving region is in contact with an analyte detection region. Lateral flow of a sample containing extracted antigens will continue from the sample receiving region to the analyte detection region. The sample receiving region and the analyte detection region may be present on a single porous member, or may comprise at least two separate porous members in lateral flow contact.

Preferably the analyte detection region contains mobile labeling reagents located at a discrete situs. These mobile labeling reagents may include an indicator labeling reagent and a control labeling reagent. The mobile indicator labeling reagent consists of a first reagent, preferably a monoclonal or polyclonal antibody, that specifically binds the analyte to be detected. Attached to the antibody, either covalently or noncovalently, is a substance or particle capable of producing a signal detected visually. Such particles used as labeling reagents can be colloidal gold, dye sols, colored latex and the like.

Preferably, the mobile indicator labeling reagent is a rabbit antibody to the carbohydrate antigen of Streptococcus Group A, and the label is colored latex (Blue).

The mobile control labeling reagent is a particle or molecule which does not bind to the indicator capture reagent and is conjugated to a substance or particle capable of producing a signal. For instance, the control labeling reagent may be BSA conjugated to colored latex (Red), while the control capture reagent is anti-BSA.

Alternatively, the control labeling reagent may be the same reagent as the indicator labeling reagent. In that embodiment, the "control capture reagent" is a reagent capable of binding the control labeling reagent but which does not bind to the antigen analyte. In that embodiment the indicator capture reagent binds to an epitope of the analyte, which is also bound by the mobile indicator labeling reagent. It is well known in the art that the carbohydrate antigen of Group A Streptococcus contains a repeated epitope. Thus, a sandwich complex can be formed even if the indicator capture reagent and the indicator labeling reagent each contain an antibody to the same epitope of Strep A.

One skilled in the art will recognize other suitable labeling particles, including gold sol particles, or other colored latex particles. One of ordinary skill in the art will also appreciate that the label can be the same on the indicator reagent and the control reagent. The indicator labeling reagent and control labeling reagent may be the same or different reagents.

The analyte detection region also preferably contains an immobile indicator capture reagent at a discrete situs. In addition, the analyte detection region also preferably contains an immobile control capture reagent at a discrete control situs.

The analyte detection region is also in lateral flow contact with an end flow region. The end flow region contains a porous material which conducts lateral flow of the liquid sample. It is capable of absorbing excess liquid sample. The end flow region may be on the same porous member as the analyte detection region, or may be a separate porous member in lateral flow contact with the analyte detection region.

In addition, in an embodiment using a test strip, the porous materials in the above aspect are laminated with one continuous or separate semi-rigid material, preferably at least 0.001 inches thick. The total thickness of all of the layers of the immunoassay device is preferably at least 0.003 inches thick. The laminate covers the back only and provides adequate mechanical strength to the device, i.e., it provides support and strength characteristics to the porous material and overall device such that lateral flow of liquid through the, device will not be interrupted, for instance by the collapse or disintegration of the device upon wetting. Additional support for the device during the immunoassay may, be provided by the walls of a test tube against which the device may rest during the lateral flow.

The term "assay chamber" refers to any liquid-proof container to which reagents can be added and into which the;, lateral flow immunochromatographic assay device can be inserted after sample extraction. Preferably the assay chamber is a test tube.

In an alternate embodiment, the assay chamber may be branched, e.g., U-shaped or V-shaped (FIG. 6), where the two branches are joined at the bottom and are in communication with the sample reservoir. The swab may be inserted into one branch of the assay chamber, while the device may be inserted into a second branch.

In still another embodiment, the assay chamber may be made of non-rigid plastic, and contain a crushable ampule containing one of the reagents. Extraction of the sample may be initiated by squeezing the tube to crush the ampule to obtain mixing of the reagents.

Alternatively, one reagent may be placed in a crushable ampule which can be inserted into the bottom of an assay chamber made of a rigid material such as plastic, glass, or metal, and the ampule may be crushed with the swab.

The term "manipulation" refers to transfer of the sample from one container to a second container or surface, and includes for example, pouring or pipetting the extracted sample from a test tube into or onto an immunoassay device. For example, manipulation of the sample following extraction may be the pouring or pipetting of the processed sample from a test tube into the plastic housing of an immunoassay device, where the processed sample contacts the lateral flow test strip of the device.

"Processing" a sample refers to exposing a solid sample or a non-homogeneous liquid sample to a reagent in order to extract, or make accessible, an analyte to the indicator labeling reagent during the lateral flow assay. By solid or non-homogeneous liquid sample is meant a sample which comprises a solid phase or a liquid sample which is adsorbed to a solid phase. Preferably, the solid or non-homogeneous liquid sample may be a swab. Preferably the swab is a throat swab.

To "extract" the analyte during processing means to make the binding site to which the labeling reagent will bind accessible to the binding agent during the lateral flow assay. This extraction may be, for instance, cleavage of the carbohydrate antigen from the cell wall of Group A Streptococcus, or disruption of cell walls or membranes to expose membrane bound analytes or intracellular analytes. Preferably the processing will extract a sufficient percent of the analyte present in the sample such that $4 \times 10^5$ cells of Group A Streptococcus/swab can be detected.

The term "analyte" as used herein refers to a compound or composition to be detected or measured in the test sample. The analyte will have at least one epitope that an antibody or an immunological reactive fragment thereof can recognize. Analyte can include any antigenic substances, haptens, antibodies and combinations thereof. The analyte of interest in an assay can be, for example, a protein, a peptide, an amino acid, a nucleic acid, a hormone, a steroid, a vitamin, a pathogenic microorganism for which polyclonal and/or monoclonal antibodies can be produced, a natural or synthetic chemical substance, a contaminant, a drug including those administered for therapeutic purposes as well as those administered for illicit purposes, and metabolites of or antibodies to any of the above substances. One preferred example of an analyte suitable for detection is the Group A Streptococcal antigen from throat swabs.

Preferably the extraction of sample is carried out in a 10×50 mm test tube (Evergreen) using a 100% rayon swab (PurFybr). Following the sample extraction, the immunoassay is initiated by inserting the device into the processed sample. The swab may be removed from the test tube or moved to the side of the test tube upon insertion of the device.

In still another embodiment, introduction of the lateral flow device into the processed sample without further sample manipulation may be indirect. For instance, the test tube may have a sealable lid which is liquid-proof when sealed, and the inner surface of the top may have the lateral flow assay device mounted at a perpendicular angle to the inner surface of the lid. When sealed, the lateral flow assay device will extend into the test tube, parallel to the sides of the test tube. After processing of the sample, the top of the test tube can be inserted into the test tube and sealed. After this introduction of the lateral flow device into the test tube, the test tube can be inverted to bring the processed sample containing the solubilized analyte into contact with the lateral flow assay device.

The term "sample" as used herein refers to any biological sample that could contain an analyte for detection which requires extraction prior to performing the immunoassay. Preferably, the sample is a throat swab sample.

As used herein, the term "sample receiving region" means the portion of the assay device which is in direct contact with the liquid sample, i.e., it receives the sample to be tested for the analyte in question. The liquid sample can then migrate, through lateral flow, from the sample receiving region towards the end flow region. Preferably the sample receiving region is the edge of the assay device. The sample receiving region in lateral flow contact with the analyte detection region. This could either be an overlap or end-to-end connection. The analyte in the sample must be capable of migrating, through lateral flow, with the liquid sample. The sample receiving region is made of porous material, usually porous paper. Preferably the sample receiving region is impregnated with buffer to neutralize the extraction reagents during the lateral flow immunoassay.

As used herein, the term "porous material" refers to any material capable of providing lateral flow. This would include material such as nitrocellulose, nitrocellulose blends with polyester or cellulose, untreated paper, porous paper, rayon, glass fiber, acrylonitrile copolymer or nylon. One skilled in the art will be aware of other porous materials that allow lateral flow. The term "lateral flow" refers to liquid flow in which all of the dissolved of dispersed components of the liquid are carried at substantially equal rates and with relatively unimpaired flow laterally through the material, as opposed to preferential retention of one or more components as would occur, e.g., in materials capable of adsorbing or imbibing one or more components.

The term "mobile" as referred to herein means diffusively or non-diffusively attached, or impregnated. The reagents which are mobile are capable of dispersing with the liquid sample and carried by the liquid sample in the lateral flow. The term "immobile" as used herein refers to reagents which are attached to the support such that lateral flow of the liquid sample does not affect the placement of the immobile particle in the discrete region of the porous material. Such attachment can be through covalent, ionic, or hydrophobic means. Those skilled in the art will be aware of means of attachment to immobilize various particles.

The term "labeling reagent" as used herein refers to any particle, protein or molecule which recognizes or binds to the analyte in question or a particle, molecule, protein which does not recognize, or bind to the analyte and has attached, conjugated or bound to it, either chemically, covalently or noncovalently, or ionicly or nonionicly any substance capable of producing a signal that is detectable by visual or instrumental means. Such labels producing a signal would include chromogens, catalysts, fluorescent compounds, colloidal metallic and nonmetallic particles, dye particles, enzymes or substrates, organic polymers, latex particles, liposomes with signal producing substances and the like. The particle or molecule recognizing the analyte can be either natural or non-natural, preferable monoclonal or polyclonal antibody.

Preferably the indicator labeling reagent is a label bound to a rabbit antibody to the Streptococcus Group A carbohydrate antigen unique to Streptococcus Group A. Preferably the label is colored latex particles or gold sol, for example, blue latex particles. In this preferred embodiment, a second control labeling reagent is BSA bound to a label, preferably colored latex particles, or gold sol, for instance, red latex particles. If desired, the label bound to the rabbit-anti Streptococcus Group A antibodies and the BSA may be the same, for instance, colored latex particles or gold sol. a signal that is detectable by visual or instrumental means. Such labels producing a signal would include chromogens, catalysts, fluorescent compounds, colloidal metallic and nonmetallic particles, dye particles, enzymes or substrates, organic polymers, latex particles, liposomes with signal producing substances and the like. The particle or molecule recognizing the analyte can be either natural or non-natural, preferable monoclonal or polyclonal antibody.

Preferably the indicator labeling reagent is a label bound to a rabbit antibody to the Streptococcus Group A carbohydrate antigen unique to Streptococcus Group A. Preferably the label is colored latex particles or gold sol, for example, blue latex particles. In this preferred embodiment, a second control labeling reagent is BSA bound to a label, preferably colored latex particles, or gold sol, for instance, red latex particles. If desired, the label bound to the rabbit-anti Streptococcus Group A antibodies and the BSA may be the same, for instance, colored latex particles or gold sol.

The term "indicator capture reagent" as used herein refers to any particle or molecule which recognizes or binds the analyte in question. The indicator capture reagent is capable of forming a binding complex with the labeling reagent that has bound to the analyte in the sample. The indicator capture reagent is immobilized to the porous material of the analyte detection region. The indicator capture reagent is not affected by the lateral flow of the liquid sample due to the immobilization to the porous material. The particle of molecule can be natural, or non-natural, i.e., synthetic. Once the capture reagent binds the analyte-indicator labeling reagent complex it prevents the analyte-indicator labeling reagent complex from continuing with the lateral flow of the liquid sample.

The term "control capture reagent" as used herein refers to any particle or molecule which is capable of binding a control labeling reagent. For example, the control labeling reagent may be BSA conjugated to a label, for example, to colored latex or gold sol. The colored latex may be, for instance, a red latex. The control capture reagent in that embodiment would be a particle or molecule which recognizes or binds the BSA conjugated to the label. In this embodiment preferably, the control capture reagent would be a monoclonal or polyclonal antibody which recognizes BSA.

Alternatively, the "control labeling reagent" may be the same as the "indicator labeling reagent". For instance, the control labeling reagent and indicator labeling reagent may be a rabbit anti-Strep A antibody linked to a label such as gold sol particles. In that embodiment, the capture reagent for the "control labeling reagent" also binds to the "indicator labeling reagent", but it does not bind the analyte. For instance, the capture reagent for the positive control signal may be anti-rabbit γ-globulin antibody, while the capture reagent for the analyte signal is an antibody to the Strep A antigen.

The control reagent is immobilized to the porous material. Once it binds the control reagent it immobilizes the labeling reagent and prevents it from continuing lateral flow with the liquid sample, giving rise to a positive control signal. Just as the capture reagent is immobilized in a discrete situs on the porous material of the analyte detection region, the control reagent is also immobilized in a discrete situs on the porous material of the analyte detection region. Binding of the immobilized capture control reagent to the control labeling reagent results in the formation of a positive control signal, which serves as an internal control that the assay was performed properly. The capture reagent for the control reagent may be applied to the porous in any geometrical shape desired.

The term "analyte detection region" as used herein refers to the portion of the assay device which is in lateral flow contact with the porous material of the sample receiving region and the end flow region. The contact can be an overlap or end-to-end connection, or the analyte detection region may be found on the same porous member as the sample receiving region and the end flow region.

The analyte in the sample must be capable of migrating through lateral flow with the liquid sample. The analyte detection region is made of a porous material just as the sample receiving region is. Preferably, the analyte detection region is made of nitrocellulose. The sample receiving region, the analyte detection region and the end flow region can be made of different material, or can be separate regions of the same porous member. The analyte detection region can contain the mobile labeling reagents, the immobile indicator capture reagent and the immobile control capture reagent. In other embodiments the analyte detection region contains only the immobilized control capture reagent and the indicator capture reagent.

The term "discrete capture situs" or "discrete control situs" as used herein refers to a defined area in which either the labeling reagents, the capture reagent or the control reagent are impregnated (for the labeling reagents) or immobilized (for the capture reagents) to the porous material. The discrete capture situs of the control or the capture reagents provide a discrete visible signal in a desired geometric shape from which to view the results of the test. For example, if the one labeling reagent is anti-analyte conjugated to label such as colored latex or gold sol, then a discrete signal will appear at the discrete capture situs if the indicator capture reagent binds and immobilizes the indicator labeling reagent complex. If the control labeling reagent is BSA conjugated to a label, such as colored latex or gold sol, then a discrete signal will form at the discrete control situs if the capture control reagent immobilizes the BSA-control labeling reagent.

The term "end flow region" as used herein refers to the portion of the assay device which is in lateral flow contact with the analyte detection region. The liquid sample migrates into the sample receiving end of the device, through the device to the opposite end flow region. The end flow region is capable of absorbing excess liquid sample. The contact with the analyte detection region can be either by overlap or end-to-end connection. Alternatively, the end flow region may be a region on the same porous member as the analyte detection region. The end flow region is made of porous material, usually porous paper.

The term "semi-rigid" as used herein refers to the material used to support the porous material of the device. This can be one continuous piece of laminate or separate pieces. The laminate is preferably vinyl but one skilled in the art will recognize that numerous materials can be used to provide the semi-rigid support. The semi-rigid material is preferably at least 0.001 inches thick. Preferably the total thickness of the immunoassay device will be 0.003 inches thick. The total thickness of the immunoassay device consists of the thickness of the backing, the membrane elements, label pads (if desired), and the cover. This minimum total thickness is required in order to produce the desired adequate mechanical strength or support for the device to function effectively.

The term "adequate mechanical strength" as used herein refers to a desired support to the assay device so as to function properly. The adequate mechanical strength is the support achieved for the entire assembled assay device so as to function properly in the collection and analysis of the analyte in the liquid sample. The minimum adequate mechanical strength is a total thickness of the device of 0.003 inches thick. This preferred measurements will provide sufficient strength and support to the porous material and assay device such that no interference with the lateral flow results, for instance from the collapse or disintegration of the device upon wetting.

The term "plastic material," or "plastic cover," or "cover" as used herein refers to any plastic material which can cover the porous material of the device. Preferably, this is mylar, however, those skilled in the art will know of various materials that can be used for such purposes. The cover can be one continuous plastic or separate pieces as shown in the figures. It must allow the discrete control and discrete capture situses to be viewed. Thus, if the cover is clear then the result can be viewed through the clear cover. If the cover is not clear, then a window, gap or hole must be used so the results can be viewed. In addition, the cover must leave a portion of the sample receiving region exposed so the sample can be applied to the receiving region.

Alternatively, the backing and plastic cover can be a molded plastic housing.

Other features and advantages of the invention will be apparent from the following detailed description of the invention in conjunction with the accompanying drawings and from the claims.

DESCRIPTION OF THE DRAWINGS

FIG. 8(a) shows a positive result. A test signal line is formed by binding of the indicator capture reagent to the indicator labeling reagent-Strep A complex. A positive control line is formed by binding of the control capture reagent to the control labeling reagent.

FIG. 8(b) shows a negative result. Only a positive control line is formed by binding of the control capture reagent to the control labeling reagent.

FIG. 8(c) shows an invalid result. If no positive control line has appeared or the background is too high and it is not possible to see the positive control signal, the result is invalid.

FIG. 9(a) shows a V-shaped assay chamber, while FIG. 9(b) shows a U-shaped assay chamber which can be used in one embodiment of this invention. In these embodiments, the swab can be inserted into one branch of the assay chamber, while the test strip is inserted into the second branch of the assay chamber.

The drawings are not necessarily to scale, and certain features of the invention may be exaggerated in scale and shown in schematic form in the interest of clarity and conciseness.

DETAILED DESCRIPTION OF THE INVENTION

The following are examples of the immunochromatographic assays of the present invention. These examples are offered by way of illustration and are not intended to limit the invention in any manner. Examples of devices are also found in U.S. Ser. No. 08/444,238, and U.S. Ser. No. 08/752,695, which are incorporated by reference.

Figure 1:
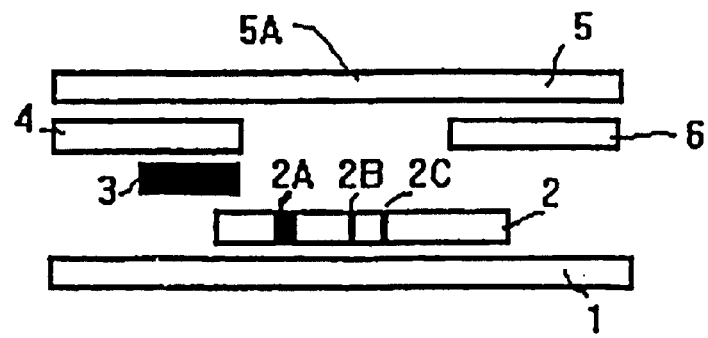
FIG. 1 illustrates an expanded perspective view of the immunochromatographic elements assembled into a test device according to a preferred embodiment of the present invention.

FIG. 1 depicts a preferred embodiment of the device used in the methods of this invention. This device does not have a plastic or cardboard casing. A series of porous material pieces (2), (3) and (4), and (6) are laminated to an elongated strip of a semi-rigid material (1), such as vinyl and the like.

The separate sample receiving region (4) is a porous material, usually paper. In this preferred embodiment shown in FIG. 1, the separate sample receiving region (4) is in direct liquid flow contact with the separate labeling reagent region (3). The separate labeling reagent region contains additional indicator labeling reagent, for instance, an antibody to the analyte bound to a label. The separate labeling reagent region also contains additional control labeling reagent. The separate labeling reagent region is preferably made of a mixture of cellulose and polyester, or other porous material.

The contact between the separate sample receiving region and the separate labeling reagent region may be perpendicular flow contact, with the separate sample receiving region placed on top of the separate labeling reagent region (not shown). The separate labeling reagent region is in direct lateral flow contact with the analyte detection region (2). The analyte detection region contains a discrete zone containing mobile indicator labeling reagent and control labeling reagent (2A). The mobile indicator labeling reagent in the analyte detection region is the same indicator labeling reagent found in the separate labeling reagent region (3), which is capable of binding to the analyte. A strip of plastic material (5), preferably clear mylar, is covered on top of the device. Portion (5A) can be a window or clear so as to permit viewing of the capture and control discrete situses, i.e., to permit viewing of the results. An end zone region (6) is in lateral flow contact with the analyte detection region.

In the embodiment shown in FIG. 1, the analyte detection region (2) of the immunochromatographic assay device contains an immobile indicator capture reagent in a discrete situs (2B) and an immobile control capture reagent at a discrete situs (2C).

Figure 2:
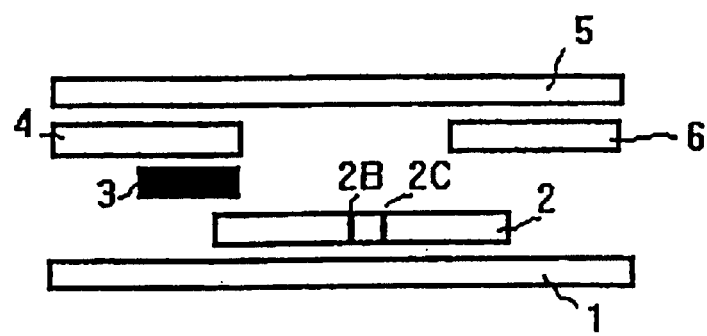
FIG. 2 illustrates an expanded perspective view of the immunochromatographic elements assembled into a test device according to an alternative preferred embodiment of the present invention.
Figure 3:
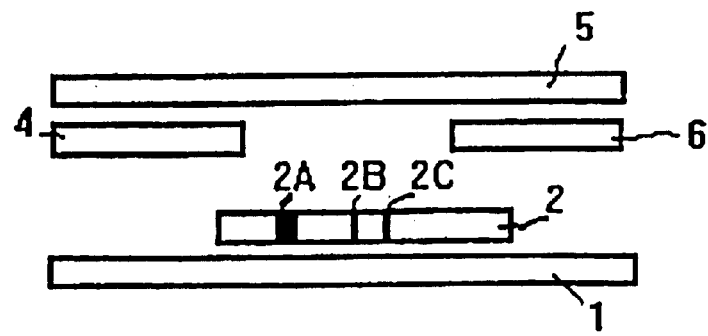
FIG. 3 illustrates an expanded perspective view of the immunochromatographic elements assembled into a test device according to another alternative preferred embodiment of the present invention.

In the embodiment shown in FIG. 2, the mobile indicator labeling reagent and control labeling reagent are found in the separate labeling reagent region, and no additional labeling reagents are placed on the membrane of the analyte detection region. In the embodiment shown in FIG. 3, there is no separate labeling reagent region. All of the mobile indicator labeling reagent and control labeling reagent are placed in the analyte detection region (2A).

The mobile labeling reagents consist of a first reagent, preferably a monoclonal or polyclonal antibody, that specifically binds the analyte to be detected. This reagent is also called the indicator labeling reagent. Attached to the antibody, either covalently or noncovalently, is a substance or particle capable of producing a signal detected visually. Such labeled particles used can be colloidal gold, dye sols, colored latex and the like. Preferably, the label is latex (Blue). One skilled in the art will recognize suitable labeling particles.

The second mobile labeling reagent is a particle or molecule which does not recognize the analyte and is conjugated to a substance or particle capable of producing a signal. This second reagent is referred to as the control labeling reagent. Preferably, the control labeling reagent is BSA conjugated to latex (Red).

In an assay, the sample receiving region (4) of the assay device is directly placed into a sample containing extracted analytes, for example, a processed throat swab sample containing extracted Streptococcus Group A carbohydrate antigen. Preferably the antigens are extracted using two or less reagents. The sample flows laterally along the porous material region by capillary action and migrates past the separate labeling reagent region (3), and then past the labeling reagents in the analyte detection region (2A) The presence and/or the amount of analyte in the sample may then be determined by the visibility of a signal line (2B) formed by the specific binding of the immobilized indicator capture reagent to the analyte-indicator labeling reagent conjugate complex.

The appearance of a second signal (2C) may be utilized as a built-in positive control signal. This positive control signal results from binding of the immobilized control capture reagent to the control labeling reagent, e.g., BSA-Red latex. If the reagents and assay are working properly, then a red signal line will appear at (2C) the discrete control situs. The red control line is an internal control. The test stick must absorb the proper amount of the sample and the test stick must be working properly for the red control line to appear. For the test stick to be working properly, the capillary flow must occur. Thus, the control line serves as an indication that the proper amount of reagents have been added to the assay chamber, and that sufficient lateral flow has occurred for the control labeling reagent to reach the control capture reagent zone.

The results of an assay can then be observed through a viewing window (5A) covered by clear mylar.

The device is required to have an adequate total mechanical strength (as defined above and discussed below) in order for the device to function without disruption of lateral flow.

Other layouts, for instance, of the upper covers or the labeled particles are possible, as long as lateral flow of the porous membranes is permitted. Overlap or end-to-end connection can be used as long as lateral flow occurs. Alternatively, the various regions of the test strip may also be placed on a single porous member.

For example, the control labeling reagent and indicator labeling reagent may be placed only in a region of the analyte detection region, and the separate labeling reagent region may be omitted. Alternatively, the control labeling reagent and the indicator labeling reagent may be placed only in a separate labeling reagent region, and additional indicator labeling reagent or control labeling reagent may be omitted from the analyte detection zone.

The assays as described above in the Summary of the Invention provide a method for antigen extraction from the sample and introduction of the device into the sample containing extracted analytes without the need for specimen manipulation following the extraction. This provides an advantage of a more rapid and convenient test procedure to the user.

| Dimensions of the Exemplary Assay Device | |
|---|---|
| Upper Covering: | 4 mm × 98 mm |
| Lower Backing: | 4 mm × 98 mm |
| Separate Labeling Reagent Region: | 4 mm × 5 mm |
| Sample Receiving Region: | 4 mm × 20 mm |
| End Flow Region: | 4 mm × 56 mm |
| Analyte Detection Region: | 4 mm × 25 mm |
| Viewing Window: | 4 mm × 9 mm |

Figure 4:
FIG. 4 illustrates an upper view of the test device constructed according to the present invention having upper covering printed with product information.
Figure 5:
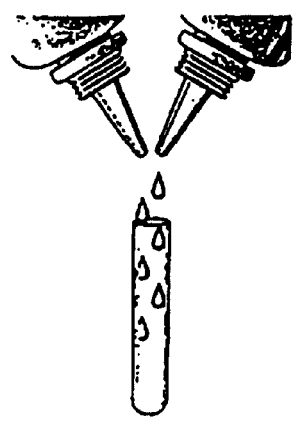
FIG. 5 illustrates the mixing of reagents in a test tube.
Figure 6:
FIG. 6 illustrates placement of a throat swab into the test tube containing the reagents.
Figure 7:
FIG. 7 illustrates the placement of the device into the test tube containing the solubilized sample.
Figure 8A:
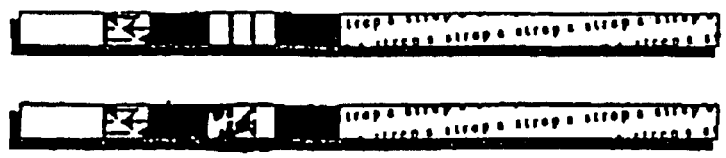
FIGS. 8(a)–(c) illustrate the interpretation of results.
Figure 8B:
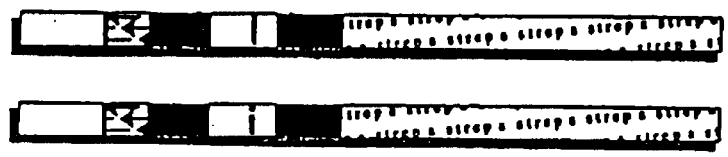
Figure 8C:
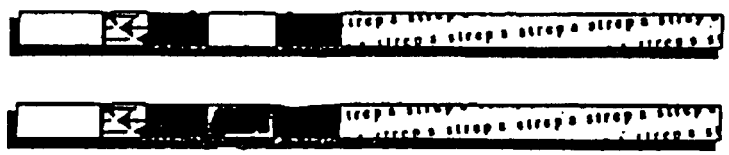
Figure 9A:
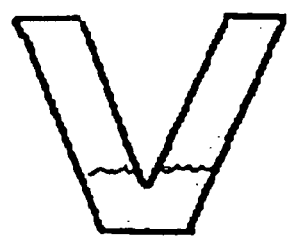
FIGS. 9(a)–(b) illustrate embodiments of branched assay chambers.
Figure 9B:
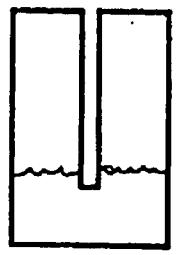
Figure 9C:
FIG. 9(c) illustrates an assay chamber containing a crushable divided ampule containing two reagents which are not mixed until the ampule is crushed.

(Note: Product information may be printed on the upper covering as shown in FIG. 4.)

In yet another aspect, the present invention comprising an immunochromatographic assay device without molded plastic casings greatly reduces the cost for manufacturing. In addition, the advantage of using a same basic design with universal applicability for different analytes also promotes the objective of inventory reduction.

EXAMPLE 1

One-Step Immunoassay for Strep A Which Does Not Require Sample Manipulation

Most preferably the one-step assay device will contain an OSOM™ Strep A Test . The OSOM™ Strep A Test detects either viable or nonviable Group A Streptococcus organisms directly from a throat swab, providing results within 5 minutes.

Specimens may be collected with a sterile swab from the tonsils and/or the back of the throat, taking care to avoid the teeth, gums, tongue or cheek surfaces. Sterile swabs may be used to collect the specimens. Preferably sterile rayon or dacron swab are used to collect specimens. Alternately, swabs with transport tubes containing liquid media can also be used. Preferably the liquid media used in transport tubes will be Modified Stuart's Transport Media ("CULTURETTE" available from Becton Dickinson).

The OSOM™ Strep A Test can be used for the qualitative detection of Group A Streptococcal antigen from throat swabs or confirmation of presumptive Group A Streptococcal colonies recovered from culture.

Materials Used and Preparation of Strep A Test:

1. Analyte Detection Region: Important features of the material are its ability to wick fluids and to bind proteins. Exemplary materials include nitrocellulose, nylon or the like. In a preferred embodiment of this invention, the material is nitrocellulose with or without laminated solid support such as polyester. Nitrocellulose is readily available from numerous suppliers.

2. Sample Receiving Region: Suitable materials include cotton, cellulose, mixed fibers, glass fiber and the like. For example, paper such as 470 and 740-E from Schleicher and Schuell, Keen, N.H., or D28 from Whatman, Fairfield, N.J., can be selected for its high fluid absorption and wicking speed. A more porous material such as glass fiber #66078 from Gelman Sciences, Ann Arbor, Mich., or "POREX" from Porex Technologies, Fairburn, Ga., is suitable for impregnating labeled particles.

3. Separate Labeling Reagent Region: A good candidate would be a porous material which allows the ease of releasing the impregnated labeling reagents from the region. Such materials include glass fiber from Gelman Sciences, Ann Arbor, Mich., or Accuwik from Pall BioSupport, Port Washington, N.Y.

4. Backing Supports: For the present invention, the preferred materials are clear mylar with thickness about 0.001 inches to 0.010 inches for the upper covering and white vinyl with thickness about 0.001 inches to 0.030 inches for the lower backing. Both the mylar and the vinyl sheets have adhesive on one side so as to attach the porous material.

Materials such as mylar, polyester, and vinyl with adhesive are readily available.

5. Labeling Reagents: A chromogenic particulate such as colored latex, colloidal gold, selenium or the like is labeled with a suitable reagent specific for the targeted analyte. For the present invention, the preferred chromogenic particulate is colored latex. More preferably, blue or red colored latex is used. Latex is commercially available from a number of sources.

6. End Zone Region: Suitable materials include cotton, cellulose, mixed fibers, glass fiber and other like materials with high fluid absorption capacity. For example, paper such as 470 and 740-E from Schleicher and Schuell, Keen, N.H., or D28 from Whatman, Fairfield, N.J., can be selected for its high fluid absorption and wicking speed.

7. Strep A antibody: New Zealand white rabbits were injected with partially purified Group A Streptococcus antigen. The rabbits which produced a high titer of antibody were identified by an enzyme immunoassay method. The sera from these rabbits were pooled and purified through Strep A antigen affinity column.

8. Anti-BSA Antibody: Affinity purified sheep anti-BSA antibody was obtained from Bethyl Lab, Montgomery Tex.

9. Preparation of Latex Conjugates

The basic protocol for conjugation of protein to latex, by simple adsorption or by covalent binding, is well known in the art and is hereby incorporated by reference.

For example, the indicator labeling reagent may be an anti-Group A streptococcus antibody conjugated with blue latex, while the indicator capture reagent may be an anti-Group A streptococcus captive antibody.

Blue carboxylated latex particles (0.2 to 0.5 microns) were activated with 0.2% 1-ethyl-3-(3dimethylaminopropyl)carbodiimide (EDAC) in the presence of 0.1% sulfo-NHS in 20 mM 2-(N-morpholino) ethanesulfonic acid (MES) buffer, pH 5.5, for 30 minutes at room temperature. The excess amount of reagents were removed by washing in an Amicon Concentrator. The activated latex particles were resuspended in 2 mM MES buffer, pH 6.5 to a concentration of 0.5%, and a ratio of 0.05 mg Strep A antibody were added to 1 mg of latex. The mixture was incubated at room temperature for 2 hours. After incubation, the conjugated latex was washed again to remove free antibody. The antibody-latex conjugate was then sonicated, filtered, and resuspended in buffer containing 20 mM Tris, pH 8.5; 20% sucrose; 0.5% casein.

The conjugation of BSA to red carboxylated latex (size of 0.2 to 0.5 microns) was essentially the same as described above except replaced the blue latex with red latex and Strep A antibody with BSA.

10. Preparation of Latex Coating Solution

The blue latex solution and the red latex solution were mixed at a ratio from 5:1 to 1:1 depends upon the sensitivity of the conjugate and intensity of red control line desired. The preferable ratio is approximate 1:1. These solutions are then impregnated into the porous material using methods well known in the art, all of which are hereby incorporated by reference.

11. Coating of Capture Reagents on the Discrete Situses of the Porous Material

Thin lines of the indicator capture reagent or control capture reagent were applied on the material using airbrush techniques (Iwata, model HP-BC2). The width of the lines can be 0.2 mm to 2 mm, a width of 1 mm is preferred. Such material is immobilized by techniques well known in the art, hereby incorporated by reference.

12. Coating of Latex Conjugate (Labeling Reagents) on the Material

Immediately after the capture reagents were applied on the material. The latex solution can be applied on the material by using airjet techniques such as BioDot Biodoser machine from Bio-Dot, Inc., Irvine, Calif. The membrane strip is then dried in a force air oven at 70° C. for 45 minutes. Such application allows the labeling reagents to be mobile.

13. Preparation of Separate Labeling Reagents Region

The separate labeling reagents region is prepared by saturating a piece of porous material such as Accuwik with the prepared latex coating solution. The soaked material is then dried in a force air oven at 70° C. for 30 minutes.

14. Preparation of Sample Receiving Region

In this invention, the sample receiving region not only absorbs and transports liquid sample, it also functions as a specimen collection apparatus and as a neutralizing agent for the acidic extraction solution. The sample receiving region may comprise a paper treated with buffer, detergents, blocking proteins and the like to facilitate movement of dried latex particles or to reduce nonspecific binding of the assay. In the case of the Strep A assay, 740E paper was soaked in a buffer solution, dried, and then assembled into the assay device. Specifically, buffer solution containing 1.5% zwittergent 3-12, definition of zwittergent 3-12 N-dodecyl-N,N-dimethyl-3-ammomio-1-propane-sulfonate 0.1% rabbit gamma globulin, 0.1 M NaCl and 0.2 M Tris, pH 9.0 was used.

15. Assembly of the Assay Device

A sheet of white vinyl (98 mm×200 mm) is placed on a flat surface. The cover paper on the white vinyl sheet is removed to expose the adhesive. A strip of the analyte detection region (25 mm×200 mm) containing latex and antibody lines is attached to the white vinyl sheet. A strip of the sample receiving region (20 mm×200 mm) is attached to the left edge of the white vinyl sheet. A separate indicator reagent region (5 mm×200 mm) is layered between the sample receiving region and the white vinyl sheet. The internal ends of the separate indicator reagent region and the sample receiving region are lying flush, and overlapping the analyte detection region by 1.5 mm. The end flow region (56 mm×200 mm) is attached to the right edge of the white vinyl sheet while overlapping about 1.5 mm on top of the analyte detection region. The cover paper from the clear mylar sheet is removed (98 mm×200 mm) to expose the adhesive. Centering the window region of the clear mylar sheet over the capture reagent lines in the analyte detection region, the clear mylar sheet is attached with the adhesive side down on top of the end flow region, analyte detection region and sample receiving region. The whole sheet is pressed with a roller to ensure the lamination is secure. The laminated sheet is then cut to 4 mm wide sticks.

Test Procedure for Running the OSOM™ Strep A Test:

Just before testing, 3 drops Reagent 1 (2M sodium nitrite) (pink) and 3 drops Reagent 2 (0.3 M acetic acid) were added to the Test Tube (the solution should turn light yellow). The swab (PurFybr Inc., Munster, Ind.) was immediately inserted into the tube. Vigorously mixing of the solution by rotating the swab forcefully against the side of the Tube at least ten times. (Best results were obtained when the specimen was vigorously extracted in the solution.) The samples were left standing for one minute. As much liquid as possible was expressed from the swab by pressing the swab firmly against the side of the Tube. The swab was discarded. An OSOM™ Strep A Test Stick was then placed into the extracted sample. The results were read at 5 minutes.

Comparison of the Sensitivity of Results of the OSOM™ Assay for Streptococcus Group A and Other One-Step Assays Procedure:

Strep A cells were picked up from a pure culture plate and suspended in saline solution. Subsequent serial dilutions were made with saline to yield different concentrations of cell suspension. The cell concentration was determined by the optical density method. $OD_{650}$ of 1 is equivalent to approximately $2 \times 10^9$ cells/mL in suspension. 25 µL of the suspension was pipetted onto the tip of each of the swabs supplied by the manufacturers. Tests were performed within 5 minutes after the swabs were spiked with cell suspension. Tests were performed by following procedure described in each prospective manufacturer's directional insert.

Results:

| Cell Qty/Swab | $4 \times 10^7$ | $4 \times 10^6$ | $8 \times 10^5$ | $4 \times 10^5$ |
| --- | --- | --- | --- | --- |
| Wyntek OSOM ™ | Positive | Positive | Weak Positive | Weak Positive |
| Quidel | Positive | Positive | Weak Positive | Negative |
| Binax | Positive | Positive | Negative | Negative |

These results indicate Wyntek OSOM™ Strep A Test can detect Group A Streptococcus cells when present at a concentration as low as $4 \times 10^5$ cells per swab, while Quidel's and Binax's tests can only detect Strep A cells when present at a concentration of $8 \times 10^5$ cells per swab or $4 \times 10^6$ cells per swab, respectively.

Performance of OSOM™ Strep A Test in Clinical Trials

In a multi-center evaluation, a total of 639 throat swabs were collected from patients presenting with pharyngitis. Each swab was inoculated to a sheep blood agar plate, then tested by the OSOM Strep A Test. Plates were incubated for 18–24 hours at 35°–37° C. at 5–10% $CO_2$ with a Bacitracin disk. Presumptive Group A Streptococcus (GAS) colonies were confirmed with commercially available Strep A testing kits.

Of the 639 total specimens, 464 were found to be negative by culture and 454 were also negative by the OSOM™ Strep A Test, for a specificity of 97.8%. Of the 175 specimens found to be positive by culture, 168 were also positive by the OSOM Strep A Test, for a sensitivity of 96.0%. The 95% confidence intervals were calculated to be 96.6–99.0% for specificity and 94.4–97.6% for sensitivity. Overall agreement between culture and the OSOM Strep A Test was 97.3% (622/639). The results are summarized below:

| Culture Classification | OSOM/Culture | % Correct |
| --- | --- | --- |
| Negative (Specificity) | 454/464 | 97.8% |
| 1 + (≦10 colonies) | 3/6 | 50.0% |
| 2 + (11–50 colonies) | 9/13 | 69.2% |
| 3 + (>50 colonies) | 44/44 | 100% |
| 4 + (predominant growth) | 112/112 | 100% |
| Total Positive (Sensitivity) | 168/175 | 96.0% |
| Total (Overall Agreement) | 622/639 | 97.3% |

In addition, the OSOM™ Strep A Test was used to confirm the identification of Group A Streptococcus on blood agar plates. As a culture confirmation test, the OSOM Strep A Test was 100% sensitive (62/62) and 100% specific (39/39).

The following organisms tested at levels of approximately $1 \times 10^8$ organisms/test were all found to be negative when tested with the OSOM Strep A Test:

| | | |
| --- | --- | --- |
| Streptococcus Group B | Enterococcus faecalis | Pseudomonas aeruginosa |
| Streptococcus Group C | Staphylococcus aureus | Bordetella pertussis |
| Streptococcus Group F | Staphylococcus epidermidis | Neisseria meningitidis |
| Streptococcus Group G | Corynebacterium diptheria | Neisseria gonorrhoeae |
| Streptococcus pneumoniae | Serratia marcescens | Neisseria sicca |
| Streptococcus sanguis | Candida albicans | Neisseria subflava |
| Streptococcus mutans | Klebsiella pneumoniae | Branhamella catarrhalis |
| | | Hemophilus influenza |

One skilled in the art will readily appreciate that the present invention is well adapted to carry out the objects and obtain the ends and advantages mentioned as well as those inherent therein. The immunological methods and devices for detecting analytes in biological samples as described herein are presently representative of preferred embodiments, are exemplary and not intended as limitations on the scope of the invention. Changes therein and other uses will occur to those skilled in the art which are encompassed within the spirit of the invention or defined by this scope with the claims.

It will be readily apparent to one skilled in the art that varying substitutions and modifications may be made to the invention disclosed herein without departing from the scope and spirit of the invention.

All patents and publications mentioned in the specifications are indicative of the levels of those skilled in the art to which the invention pertains. All patents and publications are herein incorporated by reference to the same extent as if each individual publication was specifically and individually indicated to be incorporated by reference.

We claim:

1. A method for determining the presence or absence of Streptococcus Group A antigen in a sample, comprising:
   (a) providing a lateral flow immunochromatographic device comprising a sample receiving region of porous material in liquid flow contact with a separate detection region of porous material,
      wherein said detection region comprises a mobile labeling reagent at a discrete labeling situs and an immobilized capture reagent at a discrete capture situs; and
      wherein said labeling reagent is a detectable label coupled to a binder which specifically binds to said antigen to form a labeled complex and said capture reagent specifically binds to said antigen or to said labeled complex;
   (b) providing an assay chamber which is separate from the lateral flow immunochromatographic device;
   (c) extracting said antigen from said sample with a liquid extraction solution comprising one or two extraction reagents in said assay chamber, wherein said one extraction reagent is added to the assay chamber, to form a liquid extract, or wherein said two extraction reagents are added to said assay chamber in any order, to form a liquid extract;
   (d) inserting said sample receiving region of said lateral flow immunochromatographic device into said assay chamber and contacting said liquid extract whereby said liquid extract flows through said labeling situs and then through said capture situs, without further addition of reagents or manipulation of said sample; and (e) determining the presence or absence of said antigen in said sample by detecting the presence or absence of said detectable label at said capture situs.

2. The method of claim 1 wherein said detection region further comprises both a discrete control labeling situs comprising a mobile labeling control reagent and a discrete control capture situs comprising an immobilized control capture reagent which specifically binds to and immobilizes said mobile labeling control reagent; and
wherein said method further comprises:

(f) determining the presence of said immobilized control capture reagent at said control capture situs as an internal control that the assay was performed properly.

3. The method of claim 1 wherein said sample is a throat swab sample and said extracting step further comprises contacting said throat swab sample with said extraction solution in said assay chamber for at least 10 seconds.

4. The method of claim 3 wherein said sample is a throat swab sample and said extracting step further comprises vigorously mixing said throat swab in said extraction solution in said assay chamber for at least 10 seconds.

5. The method of claim 1 wherein said extraction solution comprises 0.1–2.5 M Isodium nitrite and 0.01–1 M acetic acid.

6. The method of claim 1 wherein said two extraction reagents comprise a 0.2–5 M sodium nitrite solution and a 0.02–2 M acetic acid solution.

7. The method of claim 5 wherein the sodium nitrite solution comprises 2 M sodium nitrite and a pH color indicator reagent and the acetic acid solution has a concentration of 0.3 M, wherein the 0.3 M acetic acid solution is added to the 2 M sodium nitrite solution, and wherein said pH color indicator reagent changes color as the 0.3 M acetic acid solution is added to the 2 M sodium nitrite solution.

8. The method of claim 1 wherein said sample receiving region further comprises a buffer which neutralizes said liquid extract.

9. The method of claim 1 wherein the lateral flow side of said lateral flow immunochromatographic device is laminated to a backing support strip and the remaining side is not covered.

10. The method of claim 1 wherein the lateral flow side of said lateral flow immunochromatographic device is laminated to a backing support strip and the remaining side is partially covered with a strip of plastic material which allows the capture situs to be visible and so as to leave a portion of said sample receiving region exposed for inserting into said assay chamber and contacting said liquid extract.

11. A method for determining the presence or absence of Streptococcus antigen in a sample, comprising:

(a) providing a lateral flow immunochromatographic device comprising a sample receiving region of porous material in liquid flow contact with a separate detection region of porous material,
wherein said detection region comprises a mobile labeling reagent at a discrete labeling situs and an immobilized capture reagent at a discrete capture situs; and
wherein said labeling reagent is a detectable label coupled to a binder which specifically binds to said antigen to form a labeled complex and said capture reagent to a binder which specifically binds to said antigen or to said labeled complex;

(b) providing an assay chamber which is separate from the lateral flow immunochromatographic device;

(c) extracting said antigen from said sample with a liquid extraction solution comprising one or two extraction reagents in said assay chamber, wherein said one extraction reagent is added to the assay chamber, to form a liquid extract, or wherein said two extraction reagents are added to said assay chamber in any order, to form a liquid extract;

(d) inserting said sample receiving region into said assay chamber and contacting said liquid extract whereby said liquid extract flows through said labeling situs and then through said capture situs without further addition of reagents or manipulation of said sample; and (e) determining the presence or absence of said antigen in said sample by detecting the presence or absence of said detectable label at said capture situs.

12. The method of claim 1 or claim 11 wherein said method can detect Group A streptococcus cells when present at a concentration as low as $4 \times 10^5$ cells per said sample.

* * * * *